(12) United States Patent
Gehman et al.

(10) Patent No.: US 7,904,133 B2
(45) Date of Patent: Mar. 8, 2011

(54) WEARABLE WIRELESS DEVICE FOR MONITORING, ANALYZING AND COMMUNICATING PHYSIOLOGICAL STATUS

(75) Inventors: Stacy Earl Gehman, Seattle, WA (US); Thomas Dean Lyster, Bothell, WA (US); James Knox Russell, Bainbridge Island, WA (US); Cheryl A. Fay-Lauria, North Reading, MA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 1169 days.

(21) Appl. No.: 10/598,335

(22) PCT Filed: Feb. 2, 2005

(86) PCT No.: PCT/IB2005/050440
§ 371 (c)(1),
(2), (4) Date: Aug. 24, 2006

(87) PCT Pub. No.: WO2005/084533
PCT Pub. Date: Sep. 15, 2005

(65) Prior Publication Data
US 2008/0214901 A1   Sep. 4, 2008

(51) Int. Cl.
*A61B 5/0408* (2006.01)
(52) U.S. Cl. .......... 600/391; 600/392; 600/393; 600/509
(58) Field of Classification Search .......... 600/391–393, 600/509, 523
See application file for complete search history.

(56) References Cited

U.S. PATENT DOCUMENTS

| | | | | |
|---|---|---|---|---|
| 3,943,918 | A | * | 3/1976 | Lewis .......... 600/392 |
| 4,121,573 | A | * | 10/1978 | Crovella et al. .......... 600/382 |
| 4,669,479 | A | * | 6/1987 | Dunseath, Jr. .......... 600/391 |
| 4,809,705 | A | * | 3/1989 | Ascher .......... 600/523 |
| 6,117,077 | A | * | 9/2000 | Del Mar et al. .......... 600/301 |
| 6,315,719 | B1 | | 11/2001 | Rode et al. |
| 6,643,541 | B2 | * | 11/2003 | Mok et al. .......... 600/546 |
| 6,708,050 | B2 | * | 3/2004 | Carim .......... 600/372 |
| 2002/0045836 | A1 | * | 4/2002 | Alkawwas .......... 600/509 |
| 2003/0065253 | A1 | | 4/2003 | Stivoric et al. |
| 2003/0069510 | A1 | * | 4/2003 | Semler .......... 600/509 |
| 2006/0155183 | A1 | * | 7/2006 | Kroecker et al. .......... 600/391 |

FOREIGN PATENT DOCUMENTS

| | | |
|---|---|---|
| DE | 296 20 395 U1 | 1/1997 |
| DE | 199 05 458 A1 | 9/2000 |
| DE | 102 48 894 A1 | 5/2004 |
| EP | 0 612 498 A1 | 8/1994 |

* cited by examiner

*Primary Examiner* — Lee S Cohen

(57) ABSTRACT

A wearable compact, lightweight, noninvasive, wearable "unified" device or system (10), that does not compromise a user's motion and flexibility, detects, processes, analyzes and reports predetermined physical states of a human body. The system includes at least one pair of sense electrodes (14) and one reference electrode (16), each configured to be adhesively attached to a surface of the body (30). An electronics module (12) is in electrical communication with each of the electrodes, includes a power source, and processes and analyzes signals provided by the electrodes. The plurality of electrodes and the electronics module are covered by a single adhesive membrane (20) that enables the wearable device to adhere to the surface of the body.

17 Claims, 1 Drawing Sheet

WEARABLE WIRELESS DEVICE FOR MONITORING, ANALYZING AND COMMUNICATING PHYSIOLOGICAL STATUS

CROSS REFERENCE TO RELATED APPLICATIONS

This application claims the benefit of U.S. provisional application Ser. No. 60/548,835 filed Feb. 27, 2004, which is incorporated herein by reference.

The present invention relates generally to a wearable wireless device for monitoring and analyzing physiological conditions, and, more particularly, to a wearable wireless device, for detecting and analyzing physiological data and transmitting status data, the device constructed to be adhesively attached to a wearer of the device.

Monitoring the physiological state of an individual enables rapid detection of potentially life threatening events, particularly those that can be predicted from certain trends. To enable more continuous monitoring, devices have been developed that can be worn on the body.

However, monitoring or alarm devices that are to be worn on one's body must overcome certain design challenges. In general, a body worn device must be small and lightweight so that one can wear the device in comfort without interfering with motion and flexibility.

ECG monitoring in particular is commonly done bedside in a hospital using standard electrodes and electrode monitoring techniques. Electrode manufacturers provide adhesive electrodes that are individually attached and can be worn for up to 7 days.

One type of known ECG monitoring device, a Holter monitor, continuously monitors ECG signals, but typically only for 1 to 2 days, and requires a bulky device and cumbersome cables. More specifically, the Holter is an ECG recording device that typically comes in two different forms—a small portable tape recorder (like a walkman), or a small digital device the shape of a pager. A user wears the device on a belt around his/her waist, and four or six ECG leads extending from the device are taped to the user's chest. The device records the electrical activity of the user's heart for 24 to 48 hours (or for up to 7 days if a digital device is used). A doctor can then analyze the electrical activity and rhythm of the heart to detect any arrhythmias.

In addition to the issues presented based on the size and bulkiness of using a holter monitor, a further complication that arises with such a device is that movement of the cables that lead from the electrodes to the recording device disturb the electrode/skin interface thereby causing monitoring artifacts.

In addition to ECG monitoring, holter devices are known that also provide automatic defibrillation—again, these devices are cumbersome and present the same problems discussed above.

Finally, long term ECG monitoring and loop-recording is also possible with implantation devices, but these do not provide alarms for specific cardiac arrhythmia's, and furthermore require surgical intervention to place it on the patient. Alternatively, a looping memory monitor may be attached to the chest with two electrodes with an adhesive backing that sticks to the skin over a long period of time. However, in such a device, the electrodes have snaps on them, so that the lead wires from the monitor can be snapped on, such that during bathing or swimming, the electronic monitor device is detached, as it is not waterproof, but the adhesive electrodes remain on the chest.

The present invention is therefore directed to the problem of developing a compact, lightweight, noninvasive, wearable "unified" device or system, that does not compromise a user's motion and flexibility, for monitoring and analyzing the physiological condition of the wearer of the device and communicating an alarm condition (or physical status) upon detection thereof.

The present invention solves these and other problems by providing a wearable device for detecting, processing, analyzing and reporting predetermined physical states of a human body. The device includes a plurality of electrodes, including at least one pair of sense electrodes and a reference electrode, each configured to be adhesively attached to a surface of the body. An electronics module of the device is in electrical communication with each of the electrodes, includes a power source, and processes and analyzes signals provided by the electrodes. In accordance with the invention, the plurality of electrodes and the electronics module are covered by a single adhesive membrane which enables the wearable device to adhere to the surface of the body.

According to one embodiment of the present invention, the electronics module includes a wireless transmitter and, upon detection by the electronics module of a predetermined condition, the wireless transmitter transmits an alarm status.

In a further embodiment of the invention, the electronics module includes a battery.

The reference electrode may be a separate electrode, or may be integrally formed with the electronics module. The electronics module may also have a plurality of conductive pads formed on its top and bottom surfaces, or only its bottom surface.

In yet a further embodiment of the invention, the pair of sense electrodes and the reference electrode are integral to a breathable cloth matrix, and in yet another, the breathable cloth matrix includes electrode gel on a top surface and a bottom surface of said cloth matrix. The reference electrode may be positioned on the breathable cloth matrix between the pair of sense electrodes, and the sense electrodes may be at least two inches apart.

The present invention has the advantage of including an embodiment in which a local alarm is provided to a person wearing the device indicating that an alarm status is indicated prior to wirelessly transmitting an alarm status. In addition, one embodiment provides a device that has the advantage of including a deactivation mechanism that may be operated so as to prevent the device from wirelessly transmitting a further indication of the alarm status.

In a final illustrated embodiment, an apparatus for detecting, processing, analyzing and reporting physiological conditions includes a plurality of electrodes configured to be adhesively attached to a surface of a human body for detecting physiological data and a processor in electrical communication with each of the plurality of electrodes, the processor analyzing and processing signals provided by the plurality of electrodes into physiological output data. The electrodes and the processor are mounted together within the confines of a single flexible adhesive material adapted to be adhered to the human body, such that the electrodes and processor avoid interfering with the motion and flexibility of the human body.

These and other advantages will be apparent upon review of the detailed description in light of the following drawings.

It is worthy to note that any reference herein to "one embodiment" or "an embodiment" means that a particular feature, structure, or characteristic described in connection with the embodiment is included in at least one embodiment of the invention. The appearances of the phrase "in one embodiment" in various places in the specification are not necessarily all referring to the same embodiment.

A device in accordance with the present invention is unique in that it combines sense and reference electrodes, electronic signal acquisition, processing and analysis, a power source, and transmission of an alarm condition, all in a unified system that can be adhesively applied to the surface of the body. No other elements of the system are required to be placed on or near the patient. A variety of algorithms for analyzing various physiological conditions, and signaling alarm or status conditions, can be deployed on this platform. A device or system in accordance with the invention provides a unique combination of patient comfort, device unobtrusiveness, local signal processing and decision-making, and wireless transmission of alarm conditions, providing a breakthrough in ambulatory monitoring of infrequent but life-threatening events. The device may be adhered to the person at a variety of locations on the left anterior and left lateral surfaces of the torso, and therefore, if skin irritation becomes a problem for a particular user, the device may be repositioned as needed to avoid serious inflammation. In addition, large ECG gradients on the left anterior and collateral thorax allow acquisition of a relatively large signal with a relatively small device.

Figure 1:
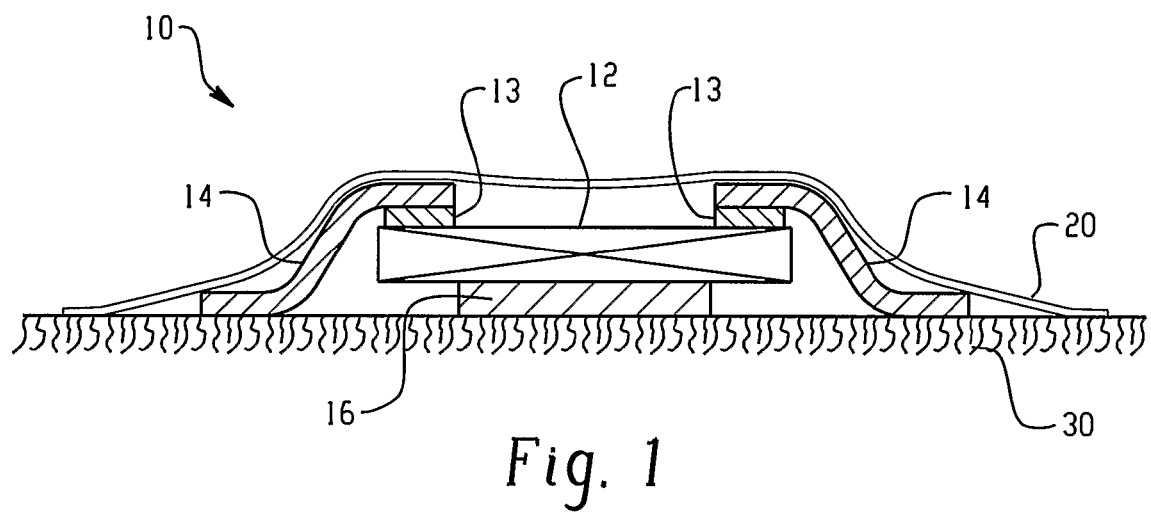
FIG. 1 illustrates an exemplary embodiment of a device for monitoring a physiological condition of a wearer according to one aspect of the present invention.

A perspective view of a wearable monitoring system 10 in accordance with the present invention is shown in FIG. 1. The elements of the system 10, shown as applied to a person's skin 30, are contained within (or covered by) an adhesive membrane 20, and include an electronics module 12 (that includes two silver plated conductive pads 13 on its top surface), at least two sense electrodes 14, and at least one reference electrode 16.

In this particular embodiment, the adhesive membrane 20 carries, or has attached thereto, the two sense electrodes 14 (as noted below, Ag/AgCl chemistry is preferred), which are then adhered to the conductive pads 13 of the electronics module 12 as illustrated in FIG. 1.

The electronics module 12 includes a power source (preferably a battery), and may contain amplifiers, analog filters, an A/D converter, a microprocessor, a memory, a transmitter and an antenna to be used by the system 10 for wireless communication.

One preferred embodiment of the electronics module 12 places the amplifiers therein for the sense electrodes 14 as close as possible to the reference electrode 16 to achieve the known advantages of an active electrode. Similarly, a very high impedance amplifier may be used in the electronics module 12 to minimize the effect of variations in skin contact with the electrode, and to minimize common mode current flow. The reference electrode 16 has a low impedance to signal ground, so that most common mode current flows through the reference electrode 16, minimizing common mode noise induced in the differential signal.

The electronics module 12 receives a signal from the sense electrodes 14 used to monitor at least one physiological condition and processes and analyzes the output. One of ordinary skill in the art will appreciate that a variety of algorithms for analyzing various physiological conditions, and signaling alarm or status conditions, may be utilized in the proposed device. For example, in one exemplary embodiment of the inventive device, certain aspects of the processing portion that may be implemented into the electronics module 12 are described in a commonly-assigned application entitled "Staged Life-Threatening Arrhythmia Detection Algorithm for Minimizing Power Consumption" US 2009/0105602 which is hereby incorporated by reference as if repeated herein in its entirety, including the drawings. FIG. 1, therein provides a block diagram of an exemplary embodiment of the processing portion. According to this embodiment, the first stage of the algorithm will detect life-threatening arrhythmias and various levels of predetermined "alarm conditions" may be implemented. For example, a low level alert may be used to indicate the detection of one or more conditions that are related to technical aspects of a heart monitoring device, a medium level alert may be used to indicate that a medical condition has been detected in the patient that may not require immediate medical attention and a high level alert may be used to indicate that a life threatening medical condition has been detected.

Analog filters in the electronics module 12 serve to eliminate frequencies that may alias into the signal band after digitization. The digitized signal is then analyzed by a microprocessor, which detects an alarm condition (e.g. ventricular fibrillation, in the case of an ECG) and generates an alarm signal, which may then be wirelessly communicated to a monitoring station (again, communication of the alarm signal may be done using any of the well known wireless technologies).

In addition, optionally, an alarm (e.g. and "audible" alarm) on the electronic module 12 may warn the wearer that an alarm condition has been detected, thereby enabling the user to cancel the alarm (via a button switch contained on the electronics module 12, for example (switch not shown)), if the alarm condition has been falsely detected.

Again, practical implementation of a wearable monitoring device dictates that the device is easy for the user to apply and is comfortable to wear. A device in accordance with the invention should not be much more complex than applying an adhesive bandage. In one preferred embodiment of the invention, the electronics module 12 may be mounted on flexible circuitry, for example, with a circuit area of about 1 inch by 2 inches (2.5 by 5 cm), or on multiple rigid circuitry pieces with flexible interconnections.

The electrodes 14 and 16 are attached closely to the electronics module 12 and the at least two sensor electrodes 14 are preferably separated by 2 inches (5 cm) or more. The entire assembly is covered by the adhesive membrane 20, which may be a flexible, waterproof, breathable, and/or biocompatible adhesive membrane to aid in adhering it to the body 30. The proposed system permits accurate monitoring of physiological status without interfering with the patient's motion and flexibility. Adhering the system 10 to the body 30 in this manner eliminates movement of the electrodes and therefore reduces artifacts that would occur due to such movement.

The electrodes 14 and 16 may be dry conductive material, such as biocompatible carbon loaded polymer, or conductive adhesive hydrogel, such as that used in standard Ag/AgCl electrocardiology electrodes. Those skilled in the art will appreciate that dry electrodes have an advantage in that the dry electrodes could be a permanent part of the electronics module 12, so that the complete device could be attached to the patient's body with a standard vapor permissible adhesive wound dressing. On the other hand, while adhesive electrodes would require a custom disposable item to be attached to the electronics module, adhesive electrodes provide the advantage of a relatively stable interface between the electrode and the skin, and therefore a lower noise ECG signal for analysis, and may not require any additional adhesive elements.

Figure 2:
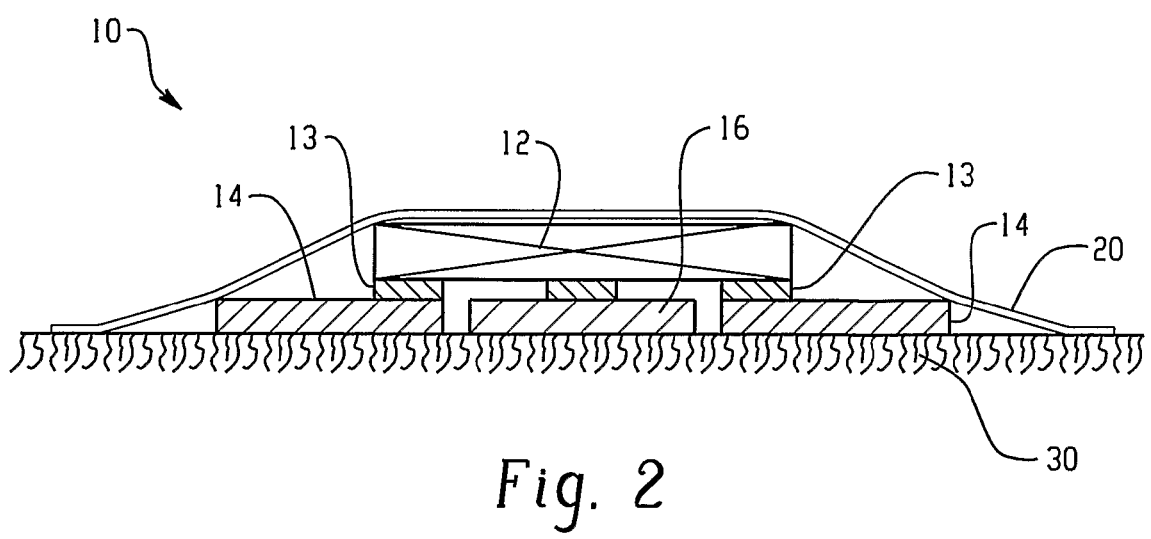
FIG. 2 illustrates another exemplary embodiment of a device for monitoring a physiological condition of a wearer according to yet another aspect of the present invention.

One embodiment of the invention, such as that illustrated in FIG. 2, includes all adhesive electrodes uses a disposable rectangular strip of material, preferably breathable cloth, with AgCl adhesive gel applied to both sides at several locations, constituting the electrodes. The disposable strip would be packaged with two release liners, similar to double-sided adhesive tape. To apply this type of wearable monitoring device, one release liner would first be removed exposing the first adhesive side of the disposable strip, and this first adhesive side would be applied to the electronics module 12, lining up the electrodes 14 and 16 with Ag conductive pads 13 on the electronics module 12. The other release liner, i.e., the second release liner, would then be removed, and the assembly would be secured to the patient's body.

Once the device electronics confirms adequate signal acquisition, adhesive membrane 20 may be applied, covering the entire assembly, more firmly attaching the assembly to the patient's body and also providing protection from the environment, e.g. from water during bathing.

In the alternative embodiment illustrated in FIG. 1, the reference electrode 16 may be a dry electrode, and the sense electrodes 14 adhesive. In this embodiment, the reference electrode 16 may be a permanent part of the electronics module 12, located on the side of the electronics module 12 facing the skin 30. A custom adhesive bandage 20 with AgCl adhesive gel electrode areas incorporated into the adhesive bandage 20 is applied to the top of the electronics module 12, lining up the adhesive gel electrodes 14 with Ag conductive pads 13 on the top of the electronics module 12. The assembly 10 is then secured to the surface 30 of the patient's body.

In yet another alternative embodiment, all of the electrodes, i.e. reference electrode 16 and sense electrodes 14, are dry conductive polymers, and only the adhesive membrane 20 provides attachment.

For adhesive gel electrodes, Ag/AgCl chemistry is preferred, i.e., conductive pads are silver plated to electronics module 12. Conductive polymer electrodes may also be implemented in this design, again either as permanent parts of the electronics module 12, or with a conductive adhesive on one side of the electrodes to adhere the electrodes to the electronics module 12.

Although various embodiments are specifically illustrated and described herein, it will be appreciated that modifications and variations of the invention are covered by the above teachings and are within the purview of the appended claims without departing from the spirit and intended scope of the invention.

The invention claimed is:

1. A wearable device for detecting, processing, analyzing and reporting predetermined physical states of a human body, the device comprising:
a plurality of electrodes, including at least one pair of sense electrodes and a reference electrode, each of said electrodes configured to make electrical connection with a surface of the body; and
an electronics module, said module in electrical communication with each of said plurality of electrodes, said module including a power source, and said module processing and analyzing signals provided by said plurality of electrodes, the reference electrode being mounted on a body facing bottom surface of the electronics module, the electronics module having at least a pair of conductive pads formed on at least one of the bottom surface and a top surface of the electronics module, the pair of sense electrodes being connected directly to the conductive pads;
a single adhesive membrane which covers the plurality of electrodes and the electronics module to enable said wearable device to adhere to the surface of the body with the reference and sense electrodes making electrical connection with the body.

2. The device of claim 1, wherein said electronics module includes a wireless transmitter and, upon detection by said electronics module of a predetermined condition, the wireless transmitter transmits an alarm status.

3. The device of claim 2, wherein said electronics module further includes a deactivation mechanism by which a user can prevent the wireless transmitter from continuing to transmit the alarm status.

4. The device of claim 3, wherein the electronics module includes a local alarm which alerts the user of the alarm status.

5. The device of claim 1, wherein said reference electrode is a dry electrode.

6. The device of claim 1, wherein at least one of the plurality of the conductive pads is silver plated on said electronics module.

7. The device of claim 1, wherein the reference electrode is positioned between the pair of sense electrodes.

8. The device of claim 7, wherein the sense electrodes are at least two inches apart.

9. A wearable device for detecting, processing, analyzing and reporting predetermined physical states of a human body, the device comprising:
a plurality of electrodes, including at least one pair of sense electrodes and a reference electrode, each of said electrodes configured to be adhesively attached to a surface of the body, said reference electrode being a dry electrode;
an electronics module, said module in electrical communication with each of said plurality of electrodes, said module including a power source, and said module processing and analyzing signals provided by said plurality of electrodes;
wherein said plurality of electrodes and said electronics module are covered by a single adhesive membrane to enable said wearable device to adhere to the surface of the body; and
wherein said reference electrode is integrally formed with said electronics module.

10. The device of claim 9, wherein said electronics module has a top surface and a bottom surface, and wherein a plurality of conductive pads are formed on at least one of the top and bottom surfaces.

11. The device of claim 9, wherein the pair of sense electrodes are integral to a breathable cloth matrix.

12. The device of claim 9, further comprising a local alarm which provides a person wearing said device an indication that an alarm status is being indicated.

13. The device of claim 12, further comprising a deactivation mechanism, operated by the wearer to prevent said device from wirelessly transmitting a further indication of the alarm status to a remote station.

14. An apparatus for detecting, processing, analyzing and reporting physiological conditions, comprising:
a pair of sensor electrodes connected at one end with a top surface of a processing module and extending to a second end which contacts a surface of a human body for detecting physiological data;
a reference electrode disposed on a bottom surface of the processing module to contact the surface of the human body under the electronics module;
the processing module analyzing and processing signals provided from electrodes into physiological output data;
wherein said plurality of electrodes and said processing module are mounted within the confines of a single flexible adhesive material adapted to be adhered to the surface of the human body, such that said electrodes and said processing module avoid interfering with the motion and flexibility of said human body.

15. The apparatus of claim 14, wherein said processing module analyzes the electrode signals for an alarm condition and the processing module further includes a transmitter which transmits an alarm signal to a remote device when the processing module detects an alarm condition.

16. The apparatus of claim 15, wherein the processing module includes a local alarm which alerts a user to the detected alarm condition.

17. The apparatus of claim 16, wherein the processing module further includes a deactivating mechanism operated by the wearer to stop transmitting the alarm signal to the remote device.

* * * * *